US008951560B2

(12) United States Patent
Vollhardt et al.

(10) Patent No.: US 8,951,560 B2
(45) Date of Patent: *Feb. 10, 2015

(54) ISOFLAVONE NANOPARTICLES AND USE THEREOF

(75) Inventors: Juergen H. Vollhardt, Ramlinsburg (CH); Philippe Emmanuel Maillan, Eschentzwiller (FR); Raphael Beumer, Loerrach (DE); Chyi-Cheng Chen, Binningen (CH); Heinz Gutzwiller, Brislach (CH); Ernst Zedi, Reinach (CH)

(73) Assignee: DSM IP Assets B.V., Heerlen (NL)

( * ) Notice: Subject to any disclaimer, the term of this patent is extended or adjusted under 35 U.S.C. 154(b) by 1555 days.

This patent is subject to a terminal disclaimer.

(21) Appl. No.: 11/994,216

(22) PCT Filed: Jan. 31, 2006

(86) PCT No.: PCT/EP2006/000827
§ 371 (c)(1),
(2), (4) Date: Apr. 30, 2008

(87) PCT Pub. No.: WO2007/000193
PCT Pub. Date: Jan. 4, 2007

(65) Prior Publication Data
US 2009/0035336 A1 Feb. 5, 2009

(30) Foreign Application Priority Data

Jun. 29, 2005 (EP) .................................... 05014096

(51) Int. Cl.
*A61K 9/14* (2006.01)
*A61K 31/352* (2006.01)
*A23K 1/16* (2006.01)
*A23L 1/30* (2006.01)
*A61K 8/49* (2006.01)
*A61K 9/10* (2006.01)
*A61K 9/51* (2006.01)
*A61Q 19/00* (2006.01)
*B82Y 5/00* (2011.01)
*A61K 8/73* (2006.01)
*A61K 9/107* (2006.01)

(52) U.S. Cl.
CPC .............. *A61K 31/352* (2013.01); *A23K 1/1618* (2013.01); *A23L 1/3002* (2013.01); *A61K 8/498* (2013.01); *A61K 9/10* (2013.01); *A61K 9/146* (2013.01); *A61K 9/5161* (2013.01); *A61Q 19/00* (2013.01); *B82Y 5/00* (2013.01); *Y10S 977/773* (2013.01); *A61K 8/732* (2013.01); *A23V 2002/00* (2013.01); *A23V 2200/25* (2013.01); *A61K 9/107* (2013.01); *A61K 2800/413* (2013.01)
USPC ........................................... 424/489; 977/773

(58) Field of Classification Search
None
See application file for complete search history.

(56) References Cited

U.S. PATENT DOCUMENTS

| 5,824,702 | A * | 10/1998 | Wei ................................ 514/456 |
| 6,251,420 | B1 * | 6/2001 | Miljkovic ...................... 424/439 |
| 6,340,470 | B1 * | 1/2002 | Tsukuda ........................ 424/439 |
| 6,677,386 | B1 * | 1/2004 | Giezen et al. ................... 516/31 |
| 8,685,456 | B2 * | 4/2014 | Beumer et al. ................ 424/489 |
| 2003/0072801 | A1 * | 4/2003 | Curatolo et al. .............. 424/465 |
| 2003/0175345 | A1 * | 9/2003 | Hite et al. ...................... 424/468 |
| 2004/0170655 | A1 | 9/2004 | Gallinat et al. |

FOREIGN PATENT DOCUMENTS

| DE | 198 25 856 | 12/1999 |
| FR | 2 817 478 | 6/2002 |
| WO | 99/38509 | 8/1999 |
| WO | WO 03068008 A1 * | 8/2003 |
| WO | 2005/044225 | 5/2005 |

OTHER PUBLICATIONS

MS Cardinali, TY (F) Lam. "New Advances in Starch-Based Particle Technologies for Aesthetic Modification." National Starch Personal Care, Presented at PCIA Manila—Mar. 2003. 11 total pages (10 numbered pages +title page).*
Muller, R.H. et al., "Nanosuspensions as Particulate Drug Formulations in Therapy Rationale for Development and What We Can Expect for the Future", Advanced Drug Delivery Reviews, No. 47, pp. 3-19, (2001), XP-002373513.
International Search Report mailed Apr. 11, 2006.
Written Opinion of the International Searching Authority mailed Apr. 11, 2006.

* cited by examiner

*Primary Examiner* — Frederick Krass
*Assistant Examiner* — Isaac Shomer
(74) *Attorney, Agent, or Firm* — Nixon & Vanderhye P.C.

(57) ABSTRACT

The present invention is directed to isoflavone nanoparticle compositions comprising isoflavone in the form of nanoparticles and preferably a carrier. The isoflavone nanoparticle compositions are particularly useful for preparing cosmetic compositions, pharmaceutical compositions, foodstuff, food and feed additives. In the compositions comprising the isoflavone nanoparticle compositions recrystallization of the isoflavone to bigger particles is retarded.

25 Claims, 16 Drawing Sheets

ISOFLAVONE NANOPARTICLES AND USE THEREOF

This application is the U.S. national phase of International Application No. PCT/EP2006/000827 filed 31 Jan. 2006 which designated the U.S. and claims priority to European Patent Application No. 05014096.1 filed 29 Jun. 2005, the entire contents of each of which are hereby incorporated by reference.

FIELD

The present invention is directed to isoflavone nanoparticle compositions comprising an isoflavone in the form of nanoparticles and preferably a carrier. The isoflavone nanoparticle compositions are particularly useful for preparing cosmetic compositions, pharmaceutical compositions, foodstuff, food additives, animal food and animal food additives. In the compositions comprising the isoflavone nanoparticle compositions recrystallization of the isoflavone to bigger particles is retarded. The isoflavone is preferably genistein.

BACKGROUND AND SUMMARY

Isoflavones are a group of vegetable dyes belonging to the flavonoids and are derived from isoflavones. The following isoflavones are particularly important:

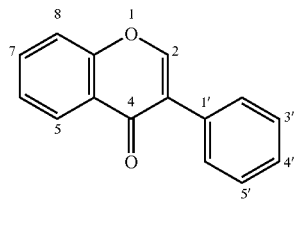 [SMILES: O=c1c(-c2ccccc2)coc2ccccc12]

|   |            | 5   | 7     | 3'  | 4'    |
|---|------------|-----|-------|-----|-------|
| 1 | Isoflavon  | H   | H     | H   | H     |
| 2 | Daidzein   | H   | OH    | H   | OH    |
| 3 | Genistein  | OH  | OH    | H   | OH    |
| 4 | Prunetin   | OH  | OCH₃  | H   | OH    |
| 5 | Biochanin A| OH  | OH    | H   | OCH₃  |
| 6 | Orobol     | OH  | OH    | OH  | OH    |
| 7 | Santal     | OH  | OCH₃  | OH  | OH    |
| 8 | Pratensein | OH  | OH    | OH  | OCH3  |

One of the most important isoflavones is genistein.

Genistein is a well-known pharmaceutically and cosmetically active ingredient which has anti-bacterial activity. Genistein is a calmodulin-antagonist, and of particular importance is the enzyme-inhibitory activity of genistein e.g. against tyrosine kinases, dopa-carboxylases, etc. Genistein can also be used in insecticides. The chemical name of genistein is 4',5,7-trihydroxyisoflavone, and the compound can be obtained by purification from natural products, such as soy products (e.g. Biochem. Biophys. Res. Commun. 179: 661-667, 1991), but it can also be chemically synthesized by methods known in the art. Genistein is commercially available from many suppliers and in a high purity. The chemical structure of genistein is as follows:

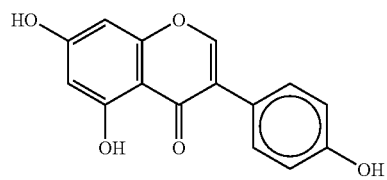

A significant number of publications are directed to genistein and the use thereof, and it can e.g. be referred to U.S. Pat. No. 5,824,702, WO 03/068218 or U.S. Pat. No. 5,948,814, to mention only three recent ones of the numerous patents and patent applications in this field.

Genistein is normally produced in crystalline powder form e.g. according to a process as disclosed in WO 2004/009576. Such a powder form has a very poor flowability. The poor powder flowability renders the crystalline powder difficult for use in making tablets and other application forms that require the powder to be free flowing. The same problem occurs if one tries to make formulations with other isoflavones.

Furthermore, it is difficult to include isoflavones, in particular genistein e.g. in food supplements in a reasonably high concentration and in a form which provides a high bioavailability of the isoflavone (or genistein).

These problems are particularly addressed in WO 99/38509, which suggests solving these problems by coupling e.g. the Genistein with an amphiphilic carrier to form a micelle having an average diameter of less than about 100 nm. The amphiphilic carriers disclosed in this document are essentially polyethyleneglycolyzed fatty acid glycerides such as those obtained from fully or partially hydrogenated various vegetable oils.

However, such micelles are difficult to obtain and their field of application is rather limited and only nutritional supplements are disclosed in WO 99/38509.

Regarding topical application forms, despite the numerous documents describing genistein and its applications, the presently marketed topical compositions with genistein either contain only very low concentrations of genistein, such as 0.01 wt.-% or less, or contain an organic solubilizer or solvent for genistein, such as ethanol. The presence of organic solvents such as ethanol in topical compositions should, however, be avoided, if possible, since some organic solvents such as ethanol can cause skin irritations.

If one prepares a topical composition which is solely based on water as a solvent and contains higher concentrations of commercially available genistein, such as more than 0.1 wt.-%, in particular more than 0.2 wt.-% or 0.5 wt.-% or more genistein, such a topical composition becomes gritty during storage. Applying such a gritty topical composition to the skin can cause irritations, and the consumer acceptance is low, in particular, if the composition is a cosmetic composition. Furthermore, together with becoming gritty the activity of the genistein in the aqueous topical formulation can decrease upon storage.

Nanosuspensions of water-insoluble pharmaceutically active compounds and methods of preparing such nanosuspensions are known in the art, and it can be referred e.g. to U.S. Pat. No. 5,858,410 and U.S. Pat. No. 5,145,684. These documents disclose many possible active ingredients which can be provided in the form of nanosuspensions, but they are quiet on genistein. Both documents are mainly concerned with a method to increase the bioavailability of a drug, and they do not address topical compositions and problems which occur in topical compositions.

Furthermore, there exist several review articles on drug nanoparticles or micron-sized drug particles, e.g. "Advanced Drug Delivery Reviews 47 (2001) 3-19". This document discloses that providing a drug in the form of nanoparticles might increase the saturation solubility and the dissolution velocity of the drug. The document is mainly concerned with the bioavailability of water-insoluble drugs which are for oral or parenteral administration. Topical formulations and problems which might occur in topical formulations are not disclosed. Genistein is not disclosed.

Another review article "Pharmaceutical Development and Technology, Vol. 9, No. 1, pages 1-13, 2004" compares the different processes for producing micron-sized drug particles and their advantages and disadvantages. According to the document, the production of small dry particles is still a challenge, and some problems are discussed which occur, in particular if the small particles are prepared by comminution of bigger dry particles and not by association of molecularly dispersed drug. While the document generally mentions that micronized drugs can be used for intravenous, topical, oral or ophthalmic compositions, the main focus is on pulmonary dry administration and improvement of the bioavailability of poorly water-soluble drugs. Apart from the above general information, topical compositions are not mentioned and genistein is not mentioned either.

Considering the wide application of isoflavones and in particular of genistein in topical and oral compositions, in solid and liquid compositions, in the pharmaceutical, cosmetic and nutritional industry, there is a need to provide isoflavones, and in particular genistein in a form which can easily be handled and formulated into all kinds of application forms, not only at a high concentration in oral compositions but also in topical compositions.

It is thus an object of the present invention to provide isoflavones and in particular genistein in a form which meets the above need.

In particular the isoflavones, such as genistein, should be provided in a form which makes it possible to prepare topical aqueous compositions, in particular topical aqueous cosmetic compositions, which are preferably free of ethanol and preferably also free of other organic solvents, and which contain the isoflavone (particularly the genistein) in a high concentration of more than 0.01 wt.-%, but preferably in even much higher concentrations such as 0.3 wt.-% or more. The compositions should be stable during storage for at least three months, preferably for at least six months, more preferably for at least one year and not develop grittyness during this time.

The isoflavones such as the genistein should also be provided in a form which is particularly suitable for food and food additives or beverages or health food such as tofu, yogurt, orange juice etc. where a high bioavailability, mixability, content uniformity, physical stability etc. must be provided.

DETAILED DESCRIPTION

Figure 1:
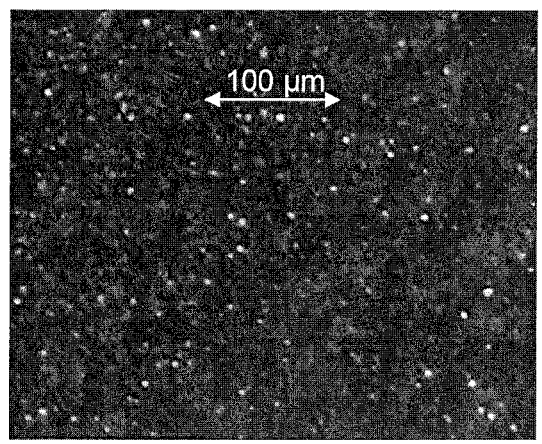
FIG. 1 shows a microscopial examination of fomulation #1 below with stabilized nanoparticles of genistein after 6 months storage at room temperature.

The present invention is based on the unexpected finding that compositions of isoflavones, in particular of genistein, wherein the isoflavone is not in the form of micelles, are stable, if the isoflavone, optionally together with a carrier and water, is micronized by certain processes to obtain a nanoparticle composition in which the particles have an average particle size of D[4.3] of 3·µm or less. Those compositions are designated herein as isoflavone or genistein nanoparticle compositions.

Thus, the present invention provides the isoflavone nanoparticle compositions and suitable processes for producing the isoflavone nanoparticle compositions.

The isoflavone nanoparticle compositions contain the isoflavone nanoparticles and optionally a carrier and, immediately after their preparation, usually water, however, it is possible to remove the water. Preferably, the compositions consist essentially
(i) of the isoflavone nanoparticles or
(ii) of the isoflavone nanoparticles and water or
(iii) of the isoflavone nanoparticles and a carrier or
(iv) of the isoflavone nanoparticles and water and a carrier.

"Consisting essentially of" means that not more than 10%, preferably not more than 5%, more preferably not more than 2% other components than the specified components are present in the compositions.

The isoflavones are not in the form of micelles as disclosed in WO 99/38509, and such micelles are not formed by the processes of the present invention and the carrier used according to the invention is preferably not an amphiphilic carrier of the type disclosed in WO 99/38509, i.e. a saturated or monounsaturated polyethyleneglycolyzed fatty acid glyceride.

Unexpectedly, the compositions of nanoparticles of an isoflavone and optionally a carrier and optionally water according to the invention can be incorporated into topical aqueous compositions such as cosmetic compositions in high concentrations of 0.3 wt.-% or more, and these topical compositions do not become gritty upon storage. The activity of the isoflavone in these topical compositions does not decrease either during storage.

The isoflavone nanoparticle compositions are preferably prepared by a high pressure homogenization process, wherein a mixture of an isoflavone, which is preferably crystalline, optionally the carrier and water is subjected to a high pressure homogenizer. Particularly preferred is furthermore a process in which a mixture of an isoflavone, which is preferably crystalline, optionally the carrier and water is subjected to an agitated bead mill. Optionally the resulting suspension is subjected to a drying process.

The compositions of nanoparticles of genistein, optionally a carrier and optionally water, which are provided by the present invention, have never been described in the prior art. In order to avoid confusing these compositions with the pharmaceutical compositions, cosmetic compositions, nutritional compositions and other compositions which are also encompassed by the present invention, the above defined compositions of nanoparticles of isoflavones optionally a carrier and optionally water will be referred to as isoflavone (or genistein) nanoparticle compositions.

The present invention also provides cosmetic compositions, pharmaceutical compositions, foodstuff, beverages, animal food, food additives, insecticides and other principally known isoflavone-containing compositions. Examples of nutritional products are tofu, yogurt, orange juice etc. Included are not only topical compositions but also oral or parenteral compositions containing the isoflavone nanoparticle compositions of the invention. Preferred are pharmaceutical compositions and cosmetic compositions, in particular aqueous topical compositions which are preferably free of ethanol, containing the isoflavone nanoparticle compositions.

The invention furthermore provides processes for producing the isoflavone nanoparticle compositions as defined above. In a preferred process a mixture of isoflavone, which is preferably crystalline, optionally the carrier and water is subjected to a high pressure homogenizer and optionally the resulting suspension is subjected to a drying process. In an even more preferred process, the isoflavone, optionally the carrier and water, is subjected to an agitated bead mill, and the resulting suspension is optionally subjected to a drying process.

The invention will be further described for genistein which is the most preferred isoflavone of the present invention. However, the further description is also valid for the other isoflavones covered by the present invention. It is of course also possible to use a mixture of more than one isoflavone, e.g. of genistein and one or more further isoflavones. The term "isoflavone" as used herein is meant to encompass all those possibilities.

The genistein nanoparticle compositions of the present invention contain genistein and preferably a carrier. The carrier is not specifically restricted and is generally added to facilitate the formation of a spray-dried powder that can be handled more easily. Without the carrier, the spray-dried powder would be very fine, resulting in low yield and high dusting. In a preferred embodiment the carrier also functions as a stabilizer to minimize the flocculation of nanoparticles in aqueous suspensions, in particular, if the stabilizer is e.g. modified starch, cellulose derivatives, gum acacia and milk protein. Generally, the carrier is selected from one or more carbohydrates, one or more proteins or a mixture of carbohydrates and proteins. Preferred carbohydrates are modified starch, sorbitol, maltose, maltodextrin, gum acacia, pectin, alginate, guar gum, xanthan, cellulose derivatives such as carboxymethylcellulose and hydroxypropylmethylcellulose and mixtures thereof. Most preferred are modified starch and mixtures comprising modified starch, and the modified starch is preferably a starch which is hydrophobically modified, so that it can act as a surfactant. An example of such a hydrophobically modified starch is starch sodium octenyl succinate, which is e.g. available under the designation "Capsul" from National Starch and Co., New Jersey, USA.

If the carrier comprises a protein, the protein is preferably selected from gelatin, milk protein, soy protein and mixtures thereof. Furthermore, mixtures of one or more carbohydrates as defined above with one or more proteins as defined above can be used, if appropriate.

Preferred carriers which are contained in the genistein nanoparticle compositions of the present invention are carriers which also have the ability to stabilize an aqueous suspension of the genistein. Such carriers generally contain a hydrophobic part and a hydrophilic part such as hydrophobically modified starch, cellulose derivatives such as hydroxypropylmethylcellulose, gum acacia and milk proteins. These carriers/stabilizers are preferred components of the genistein nanoparticle compositions of the present invention.

However, it should be understood that it is not essential for the invention that the carrier also has a stabilizing function on suspensions of the genistein. The genistein nanoparticle compositions of the invention are preferably used in topical, pharmaceutical or cosmetic compositions which might already contain suspension stabilizers (or the formulation process alone is adequate to resuspend the genistein nanoparticles), and therefore, the presence of a suspension stabilizer in the genistein nanoparticle compositions of the invention is not absolutely necessary. However, if the genistein nanoparticle compositions of the invention already contain a carrier which has also suspension stabilizing activity, it might be possible to reduce the amount of suspension stabilizer in the topical cosmetic or pharmaceutical composition which is prepared with the genistein nanoparticle compositions of the invention. The genistein nanoparticle compositions of the invention are usually prepared as aqueous suspensions containing genistein, a carrier and water. In a preferred embodiment the aqueous suspensions are then subjected to a suitable drying method such as spray-drying or freeze-drying to eliminate most or all of the water and to obtain a granular or powdery product. According to the present invention both compositions are preferred, the aqueous suspensions containing genistein, water and optionally a carrier and the dry compositions containing genistein and optionally a carrier. Thus, in a preferred embodiment the compositions of the invention consist of genistein, a carrier and optionally water. It should be understood that the term carrier as used therein includes a mixture of several different carriers as defined above.

If the genistein nanoparticle compositions of the present invention are powder compositions or granular compositions, they comprise preferably at least 1 wt.-% of genistein, preferably 20 wt.-% or more, more preferably 50 wt.-% of genistein or more with 90 wt.-% of genistein or more also being preferred. The rest of the genistein nanoparticle compositions is the optional carrier and, depending on the drying process, residual water which is not removed from the genistein nanoparticle composition. Thus, preferably the genistein nanoparticle composition contains 99 wt.-% or less of carrier and, if applicable, residual water, preferably 80 wt.-% or less, more preferably 50 wt.-% or less of carrier and, if applicable, residual water, and 10 wt.-% or less of carrier and, if applicable, residual water is also preferred. Preferably the genistein nanoparticle compositions of the present invention contain at least 1 wt.-% of carrier and, if applicable, residual water, preferably the genistein nanoparticle compositions of the present invention contain 5 wt.-% or more of carrier and, if applicable, residual water. Preferred granular or powder genistein nanoparticle compositions contain genistein in an amount from 1 to 99 wt.-%, from 30 to 95 wt.-%, from 30 to 95 wt.-%, from 50 to 95 wt.-%, from 70 to 95 wt.-%, from 70 to 90 wt.-%, from 90 to 99 wt.-%, from 90 to 95 wt.-%, the rest being carrier and, if applicable, residual water. Of course, compositions not containing a carrier but only genistein and, if applicable, residual water are also preferred. The genistein nanoparticle compositions in the form of a powder can be prepared from the aqueous suspensions described below by a conventional spray drying process or a freeze drying process.

If the genistein nanoparticle composition of the present invention is in the form of an aqueous suspension containing genistein, optionally a carrier and water, the amount of water is not particularly restricted, but generally these aqueous compositions will contain 0.5% or more, preferably 3% or more, preferably 5% or more of genistein and optionally a carrier, more preferably 10% or more, more preferably 20% or more, 30% or more, 40% or more or 50% or more of genistein and optionally carrier, the rest being water, wherein the relative amounts of genistein and carrier are as defined above. The minimum amount of water which is present in the aqueous suspensions is the amount necessary to form a suspension. The aqueous suspensions of the invention can be directly obtained from the production process and in this case the amount of solid particles in the suspension and thus also the amount of water in the suspension depends on the equipment which is used for preparing the suspension. If a higher solids content should be provided, it is possible to remove water from the aqueous suspension as required, e.g. by evaporation, preferably at constant temperature. Preferred are aqueous suspensions which are directly obtained by high pressure homogenization or by agitated ball milling (wet grinding) of genistein and optionally a carrier, and such suspensions usually contain 40% or more of water. Aqueous suspensions which contain 50% or more of water, the rest being genistein and optionally a carrier in relative amounts as defined above, are also preferred.

Preferred compositions are also compositions containing genistein in an amount in the range of 10 to 50 wt.-% and carrier in an amount of a ratio of genistein to carrier in the range of 10:1 to 1:10, preferably 10:1 to 1:1 or 1:1 to 1:5 such as about 1:2, the rest of the composition being water, such as compositions containing 25% of genistein, 5% of carrier and 70% of water. Preferred are also compositions containing 10 to 30% of genistein (preferred 15 to 25% of genistein, particularly about 20% of genistein), 15 to 40% of carrier (preferred 20 to 30% of carrier, particularly about 25% of carrier) and the rest being water.

An important feature of the genistein nanoparticle compositions of the invention is the particle size of the genistein, which is 3 μm or less, preferably 1 μm or less, such as about 0.5 μm. Preferred ranges of the average particle size of the genistein in the genistein nanoparticle compositions of the invention are 0.05 to 3 μm, more preferred 0.05 to 1 μm, still more preferred 0.05 to 0.5 μm. Furthermore, a particle size of 0.3 to 1.0 μm is preferred. Preferred are also the above ranges with 0.1 instead of 0.05 as lower limit for the average particle size. All particle sizes above are average particle sizes D[4,3], i.e. volume mean diameters or De Brouckere mean diameters. Preferably, the particle size of the genistein particles according to D[3,2] are within the ranges of 0.05 to 0.5, preferably of 0.1 to 0.2, where D[3,2] is the surface mean diameter or the sauter mean diameter. All measurements of particle size referred to in this specification are made by laser diffraction technique using a "Matersizer 2000" of Malvern Instruments Ltd., UK, and further information on the above particle sizes D[4,3] and D[3,2] can e.g. be found in "Basic principles of particle size analytics", Dr. Alan Rawle, Malvern Instruments Limited, Engima Business Part, Grovewood Road, Malvern, Worcestershire, WR14 1XZ, UK and the "Manual of Malvern particle size analyzer".

Applicants do not wish to be bound by theory, and it is not known whether the particles in the carrier containing genistein nanoparticle composition of the present invention contain a mixture of genistein and carrier, which means that genistein and the carrier are present in the same particle, or whether particles of genistein and particles of carrier are independently present in the genistein nanoparticle compositions. It is also possible that the genistein nanoparticle composition contains particles which consist solely of genistein, particles which comprise both genistein and carrier and particles which consist solely of carrier. All these possibilities are included within the present invention, and if the genistein nanoparticle compositions of the present invention comprise particles which contain both genistein and carrier, the above particle size refers to the particle as such comprising both genistein and the carrier.

If nothing else is stated, in this application parts and percentages are per weight and are based on the weight of the composition.

The genistein nanoparticle compositions of the invention can be used for all purposes for which genistein has been used in the prior art, but in particular genistein nanoparticle compositions of the present invention are for use in pharmaceutical compositions, cosmetic compositions, foodstuff, animal food or food additives with food additives and cosmetic compositions being most preferred.

The compositions of the invention containing the genistein nanoparticle compositions of the invention in their broadest sense are referred to as "general compositions" in the following.

Preferably, the general compositions of the present invention are topical compositions, such as liquid or solid oil-in-water emulsions, water-in-oil emulsions, multiple emulsions, microemulsions, PET-emulsions, bickering emulsions, hydrogels, alcoholic gels, lipogels, one or multiphase solutions, foams, ointments, plasters, suspensions, powders, crèmes, cleanser, soaps and other usual compositions, which can also be applied by pens, as masks or as sprays.

The general compositions of the invention can also contain usual cosmetic adjuvants and additives, such as preservatives/antioxidants, fatty substances/oils, water, organic solvents, silicones, thickeners, softeners, emulsifiers, sunscreens, cosmetic actives antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, e.g. those suited for providing a photoprotective effect by physically blocking out ultraviolet radiation, or any other ingredients usually formulated into cosmetics.

The general composition of the present invention can also contain one or more additional pharmaceutically or cosmetically active ingredients, in particular bisabolol, alkyldiols such as 1,2-pentandiol, hexanediol or 1,2-octanediol, vitamins, panthenol, phytol, phytantriol, ceramides and pseudoceramides, amino acids and bioactive peptides, protein hydrolysates, AHA acids, polyunsaturated fatty acids, plant extracts, DNA or RNA and their fragmentation products or carbohydrates.

Additionally the general composition of the present invention may contain UV-A and UV-B filters. Examples of UV-B or broad spectrum screening agents, i.e. substances having absorption maximums between about 290 and 340 nm, which are preferred for combination with the compounds of the present invention, are the following organic and inorganic compounds:

Acrylates such as 2-ethylhexyl 2-cyano-3,3-diphenylacrylate (octocrylene, PARSOL® 340), ethyl 2-cyano-3,3-diphenylacrylate and the like;

Camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like;

Cinnamate derivatives such as octyl methoxycinnamate (PARSOL® MCX), ethoxyethyl methoxycinnamate, diethanolamine methoxycinnamate (PARSOL®

Hydro), isoamyl methoxycinnamate and the like as well as cinnamic acid derivatives bond to siloxanes;

p-Aminobenzoic acid derivatives, such as p-aminobenzoic acid, 2-ethylhexyl p-dimethylaminobenzoate, N-oxypropylenated ethyl p-aminobenzoate, glyceryl p-aminobenzoate, Benzophenones such as benzophenone-3, benzophenone-4, 2,2', 4,4'-tetrahydroxy-benzophenone, 2,2'-dihydroxy-4,4'-dimethoxybenzophenone and the like;

Esters of Benzalmalonic acid such as di-(2-ethylhexyl) 4-methoxybenzalmalonate;

Esters of 2-(4-ethoxy-anilinomethylene)propanedioic acid such as 2-(4-ethoxy anilinomethylene)propanedioic acid diethyl ester as described in the European Patent Publication EP 0895 776;

Organosiloxane compounds containing benzmalonate groups as described in the European Patent Publications EP 0358584 B1, EP 0538431 B1 and EP 0709080 A1, in particular Parsol SLX;

Drometrizole trisiloxane (Mexoryl XL);

Pigments such as microparticulated TiO2, and the like. The term "microparticulated" refers to a particle size from about 5 nm to about 200 nm, particularly from about 15 nm to about 100 nm. The TiO2 particles may also be coated by metal oxides such as e.g. aluminium or zirconium oxides or by organic coatings such as e.g. polyols, methicone, aluminium stearate, alkyl silane. Such coatings are well known in the art.

Imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like.

Salicylate derivatives such as isopropylbenzyl salicylate, benzyl salicylate, butyl salicylate, octyl salicylate (NEO HELIOPAN OS), isooctyl salicylate or homomethyl salicylate (homosalate, HELIOPAN) and the like.

Triazine derivatives such as octyl triazone (UVINUL T-150), dioctyl butamido triazone (UVASORB HEB), bis ethoxyphenol methoxyphenyl triazine (Tinosorb S) and the like.

Examples of broad spectrum or UV A screening agents i.e. substances having absorption maximums between about 320 and 400 nm, which are preferred for combination with the compounds of the present invention are the following organic and inorganic compounds:

Dibenzoylmethane derivatives such as 4-tert. butyl-4'-methoxydibenzoyl-methane (PARSOL® 1789), dimethoxydibenzoylmethane, isopropyldibenzoylmethane and the like;

Benzotriazole derivatives such as 2,2'-methylene-bis-(6-(2H-benzotriazole-2-yl)-4-(1,1,3,3,-tetramethylbutyl)-phenol (TINOSORB M) and the like;

Phenylene-1,4-bis-benzimidazolsulfonic acids or salts such as 2,2-(1,4-phenylene)bis-(1H-benzimidazol-4,6-disulfonic acid) (Neoheliopan AP);

Amino substituted hydroxybenzophenones such as 2-(4-Diethylamino-2-hydroxy-benzoyl)-benzoic acid hexylester as described in the European Patent Publication EP 1046391;

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g., 3,3-Diphenylacrylate derivatives as described in the European Patent Publications EP-A 0 514 491 and EP-A 0 780 119;

Benzylidene camphor derivatives as described in the U.S. Pat. No. 5,605,680;

Organosiloxanes containing benzmalonate groups as described in the European Patent Publications EP-A 0358584, EP-A 0538431 and EP-A 0709080, in particular Parsol SLX.

A good overview of UV-A and UV-B-filters which can be added to the compositions of the present invention can also be found in DE-A 103 27 432. All UV-filter compounds disclosed in this document are also useful as components for the compositions of the present invention and are included herein by reference.

The general compositions of the present invention preferably contain one or more antioxidants/preservatives. Based on the invention all known antioxidants usually formulated into cosmetics can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, y-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinsulfoximine, buthioninsulfone, penta-, hexa-, heptathioninsulfoximine) in very low compatible doses (e.g. pmol to μmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetra-isopalmitate, Mg-ascorbylphosphate, Na-ascorbylphosphate, ascorbylacetate), tocopherol and derivates (such as vitamin-E-acetate), mixtures of nat. vitamin E, vitamin A and derivatives (vitamin-A-palmitate and -acetate) as well as coniferylbenzoate, rutinic acid and derivatives, α-glycosylrutin, ferulic acid, furfurylidenglucitol, carnosine, butylhydroxytoluene, butylhydroxyanisole, trihydroxybutyrophenone, urea and its derivatives, mannose and derivatives, zinc and derivatives (e.g. ZnO, $ZnSO_4$), selenium and derivatives (e.g. selenomethionine), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 wt. % to about 10 wt. % of the total weight of the composition of the present invention. Preferably, one or more preservatives/antioxidants are present in an amount about 0.1 wt. % to about 1 wt. %.

Typically topical formulations also contain surface active ingredients like emulsifiers, solubilizers and the like. An emulsifier enables two or more not miscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/C10-30 alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/C10-30-alkyl acrylate crosspolymer, PEG-20 sorbitan isostearate, sorbitan isostearate, and mixtures thereof. The one or more emulsifiers are present in a total amount about 0.01 wt. % to about 20 wt. % of the total weight of the composition of the present invention. Preferably, about 0.1 wt. % to about 10 wt. % of emulsifiers are used.

The lipid phase of the topical compositions can advantageously be chosen from:
mineral oils and mineral waxes;
oils such as triglycerides of caprinic acid or caprylic acid, preferable castor oil;
oils or waxes and other natural or synthetic oils, in an preferred embodiment esters of fatty acids with alcohols e.g. isopropanol, propylene glycol, glycerin or esters of fatty alcohols with carboxylic acids or fatty acids;
alkylbenzoates; and/or
silicone oils such as dimethylpolysiloxane, diethylpolysiloxane, diphenylpolysiloxane, cyclomethicones
and mixtures thereof.

Exemplary fatty substances which can be incorporated in the oil phase of the emulsion, micro-emulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyidodecylmyristate, cetearylisononanoate, isopropyl-myristate, isopropylpalmitate, isopropylstearate, isopropyloleate, n-butylstearate, n-hexyllaureate, n-decyloleate, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the topical compositions of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotri-siloxane, polydimethylsiloxane, poly(methylphenylsiloxane) and mixtures thereof.

Other fatty components which can advantageously be incorporated in topical compositions of the present invention are isoeikosane; neopentylglycoldiheptanoate; propylenglycol-dicaprylate/dicaprate; caprylic/capric/diglycerylsuccinate; butyleneglycol caprylate/caprate; C12-13-alkyllactate; di-C12-13 alkyltartrate; triisostearin; dipentaerythrityl hexacaprylat-/hexacaprate; propyleneglycolmonoisostearate; tricaprylin; dimethylisosorbid. Especially beneficial is the use of mixtures C12-15-alkylbenzoate and 2-ethylhexylisostearate, mixtures C12-15-alkylbenzoate and isotridecylisononanoate as well as mixtures of C12-15-alkylbenzoate, 2-ethylhexylisostearate and isotridecylisononanoate.

The oily phase of the compositions of the present invention can also contain natural vegetable or animal waxes such as bee wax, china wax, bumblebee wax and other waxes of insects as well as shea butter and cocoa butter.

A moisturizing agent may be incorporated into a topical composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimethicone, cyclomethicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of C9-15-alcohols, isononyl iso-nonanoate, ethers such as polyoxypropylene butyl ethers and polyoxypropylene cetyl ethers, and C12-15-alkyl benzoates, and mixtures thereof. The most preferred emollients are hydroxybenzoate esters, aloe vera, C12-15-alkyl benzoates, and mixtures thereof. An emollient is present in an amount of about 1 wt. % to about 20 wt. % of the total weight of the composition. The preferred amount of emollient is about 2 wt. % to about 15 wt. %, and most preferably about 4 wt. % to about 10 wt. %.

Moisturizers that bind water, thereby retaining it on the skin surface are called humectants. Suitable humectants can be incorporated into a topical composition of the present invention such as glycerin, polypropylene glycol, 1,2-pentandiol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a composition of the present invention, preferably about 1 wt. % to about 5 wt. %.

The aqueous phase of the preferred topical compositions of the present invention can contain the usual cosmetic or pharmaceutical additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or -monobutylether, diethyleneglycol monomethyl- or -monoethylether and analogue products, polymers, foam stabilizers; electrolytes and especially one or more thickeners. Thickeners that may be used in formulations of the present invention to assist in making the consistency of a product suitable include carbomer, siliciumdioxide, magnesium and/or aluminium silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof. Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the composition of the present invention, preferably, 1 wt. % to about 5 wt. %.

The addition of electrolytes into the composition of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the composition of the present invention.

The topical compositions of the invention can preferably be provided in the form of a lotion, a thickened lotion, a gel, a cream, a milk, an ointment, a powder or a solid tube stick and can be optionally be packaged as an aerosol and can be provided in the form of a mousse, foam or a spray. The compositions according to the invention can also be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

Particularly preferred are cosmetic and pharmaceutical compositions, still more preferred are cosmetic compositions.

The term "cosmetic preparation" or "cosmetic composition" as used in the present application refers to cosmetic compositions as defined under the heading "Kosmetika" in Römpp Lexikon Chemie, 10th edition 1997, Georg Thieme Verlag Stuttgart, New York.

The cosmetic or pharmaceutical compositions of the present invention contain the genistein nanoparticle compositions of the present invention together with cosmetically or pharmaceutically acceptable excipients or diluents. If nothing else is stated, the excipients, additives, diluents, etc. mentioned in the following are suitable for both pharmaceutical and cosmetic compositions.

The topical cosmetic and pharmaceutical compositions of the present invention preferably comprise more than 0.01%, preferably 0.1% or more, more preferably 0.2% or more of the nanoparticles of genistein and optionally a carrier. However, the effect which is achieved by incorporating the genistein nanoparticle compositions into the topical cosmetic and pharmaceutical compositions is most impressive in pharmaceutical and cosmetic compositions containing 0.3% or more of genistein, because at these high concentrations the topical pharmaceutical and cosmetic compositions of the present invention have a particularly low increase in the particle size of the genistein nanoparticles during storage (and sometimes there is even a decrease). The effect at such high concentrations is much more pronounced than at lower concentrations of less than 0.3%, which is particularly surprising and advantageous, because it allows the provision of cosmetic and pharmaceutical compositions having very high concentrations of genistein, which could not be obtained using prior art genistein compositions. Therefore, the cosmetic and pharmaceutical compositions of the invention will contain the nanoparticles containing Genistein and optionally a carrier in a concentration of preferably 0.3% or more, more preferably 0.5% or more. The following ranges of nanoparticles of genistein and optionally carrier are also preferred: 0.3% to 3%, 0.3% to 2%, 0.3% to 1% and the above ranges, where the lower limit is 0.4 or 0.5% instead of 0.3%.

Regarding the kind of the topical cosmetic and pharmaceutical composition and the preparation of the topical cosmetic and pharmaceutical preparations as well as for further suitable additives, it can be referred to the pertinent literature, e.g. to Novak G. A., Die kosmetischen Präparate—Band 2, Die kosmetischen Präparate—Rezeptur, Rohstoffe, wissenschaftliche Grundlagen (Verlag für Chem. Industrie H. Ziolkowski KG, Augsburg).

It is furthermore possible to include the genistein nanoparticle compositions of the present invention into oral cosmetic and pharmaceutical composition, e.g. in the form of pills, tablets, capsules that may contain granules or pellets, as a liquid, oral formulation or as an additive to foodstuff as is generally known to a skilled person. Useful procedures and useful additives for preparing oral compositions are e.g. disclosed in the standard literature Remington: The Science and Practice of Pharmacy, Lippincot, Williams & Wilking (Editors) 2000, which is included herein by reference. It is preferred to incorporate the compositions of the present invention into foodstuff and in particular into animal food, more particularly into pet food. How to prepare such foodstuff is known in the art.

As usual additives for oral compositions, in particular for tablets, usual excipients such as microcrystalline cellulose, sodium citrate, calcium carbonate, disodium or dipotassium phosphate, sodium or potassium phosphate, glycine, disintegration agents such as starch or alginic acid, binders such as polyvinylpyrolidone, saccharose, gelatin and gum arabic, lubricants such as magnesium stearate, sodium lauryl sulfate or talcum can be used. If the compositions are filed into gelatin capsules, usual additives for the preparation of granules are lactose or lactate as well as polyethylene glycols with a high molecular weight. Further additives and excipients as well as additives and excipients for other oral formulations and for food additives are known to a skilled person, and it can be referred to the pertinent literature such as "Grundzüge der Lebensmitteltechnik", Horst Dieter Tscheuschner (Editor), 2. Edition, Hamburg, Beers 1996.

The composition can also contain one or more additional pharmaceutically or cosmetically active ingredients, in particular for preventing or reducing acne, wrinkles, lines, atrophy, inflammation, as well as topical anesthetics, artificial tanning agents and accelerators, antimicrobial agents, and antifungal agents and sunscreen additives.

Examples are peptides (e.g., Matrixyl™ [pentapeptide derivative]), glycerol, urea, guanidine (e.g., amino guanidine); vitamins and derivatives thereof such as ascorbic acid, vitamin A (e.g., retinoid derivatives such as retinyl palmitate or retinyl propionate), vitamin E (e.g., tocopherol acetate), vitamin $B_3$ (e.g., niacinamide) and vitamin $B_5$ (e.g., panthenol) and the like and mixtures thereof, wax-based synthetic peptides (e.g., octyl palmitate and tribehenin and sorbitan isostearate and palmitoyl-oligopeptide), anti-acne medicaments (resorcinol, salicylic acid, and the like); antioxidants (e.g., phytosterols, lipoic acid); flavonoids (e.g., isoflavones, phytoestrogens); skin soothing and healing agents such as aloe vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol), desquamatory actives, anti-acne actives, vitamin $B_3$ compounds, anti-oxidants, peptides, hydroxy acids, radical scavengers, chelators, farnesol, anti-inflammatory agents, topical anesthetics, tanning actives, skin-lightening agents, anti-cellulites agents, flavonoids, antimicrobial actives, and antifungal actives, in particular bisabolol, alkyldiols such as 1,2-pentanediol, hexanediol or 1,2-octanediol, vitamins, panthenol, phytol, phytanetriol, ceramides and pseudoceramides, amino acids and bioactive peptides, protein hydrolysates, AHA acids, polyunsaturated fatty acids, plant extracts, DNA or RNA and their fragmentation products or carbohydrates, biotin, conjugated fatty acids, carnitin, vitamin E, A, C, B3, B6, B12, oligopeptides, carnosine, biochinonen, phytofluen, phytoen, folic acid, and their corresponding derivatives.

The content of the genistein in the oral cosmetic and pharmaceutical compositions of the present invention is usually about 0.1% to 90%, preferably about 1% to 80%. Typically in pharmaceutical compositions, such as a tablet, the genistein can go as high as 50%, but preferably it is in the 1%-10% range. The application is such that the desired effect occurs and depends on the patient and the desired effect. A usual daily dosage can be in a range from about 1 mg/day to 1 g/day, e.g. about 5 mg/day to 100 mg/day.

The cosmetic and pharmaceutical compositions of the present invention can also be in the form of injectable compositions, in particular if the compositions are for promoting hair growth. The preparation of injectable cosmetic and pharmaceutical compositions is known to a skilled person, and it can be referred to the pertinent literature, in particular to Remington already cited above.

According to the invention nutritional products containing the genistein nanoparticle compositions of the invention are also preferred, such as yogurt, tofu, fruit juices such as orange juice, etc. The content of the genistein nanoparticles is not particularly restricted, but usually the content of genistein in these products is 0.01% or more, preferably 0.1% or more, but generally not higher than 10% or 5%. The oral pharmaceutical and nutritional products of the present invention have the particular advantage that the genistein has a high bioavailability combined with an unexpected high physical stability (the genistein particles do not grow to an unacceptable size).

The genistein nanoparticle compositions of the present invention are preferably obtained by fragmentation of genistein crystals and optionally the carrier in a high pressure homogenizer. The genistein nanoparticle compositions of the present invention are more preferably obtained by milling genistein (in particular genistein crystals) and optionally carrier in an agitated bead mill. The fragmentation and milling is usually carried out with an aqueous suspension.

Suitable homogenizers are known in the prior art and commercially available and for example it can be referred to DeBEE 2000 high pressure homogenizer of B.E.E. International Ltd., Migdal Haemek, Israel. The homogenizer is preferably operated at a pressure from 500 bar to 4000 bar, more preferably at a pressure from 500 bar to 3000 bar, most preferably at a pressure from 500 bar to 2000 bar. Preferably, the homogenizer is equipped with a nozzle system as disclosed in EP-A 1 008 380.

Preferably the genistein and the carrier are cycled through the high pressure homogenizer 1 to 200 times, more preferably 5 to 100 times, such as 5 to 30 times. The required number of cycles can easily be found by some routine experiments.

In a particularly preferred embodiment first the genistein without the carrier is subjected to a homogenization in a high pressure homogenizer, for example for 5 to 100 times, such as 5 to 30 times, then a solution of the carrier is added and homogenization is continued for example for further 1 to 50, such as 1 to 10 cycles. If necessary, the number of cycles can be increased.

It is believed that during homogenization the genistein crystals are fragmented mostly by cavitation and shearing created in the high pressure process, and the aqueous nanosuspension which is processed can have a solid content of up to 50% or even more. The aqueous nanosuspension can be used as such for preparing the pharmaceutical or cosmetic compositions of the present invention or it can first be subjected to a drying step in order to obtain a powder or granular composition consisting essentially of genistein, optionally the carrier and eventually residual water which is not removed by the drying process. The drying can be done by usual processes such as spray-drying or freeze-drying.

The genistein nanoparticle compositions of the present invention are most preferably obtained by fragmentation in an agitated bead mill by a wet grinding process. Suitable wet grinding mills are known in the prior art and commercially available and for example it can be referred to Netzsch LMZ 4 wet grinding mill of NETZSCH-Feinmahltechnik GmbH, Sedanstraße 70, 95100 Selb, Germany. Preferably the genistein and optionally the carrier are cycled through the agitated bead mill 1-50 times, more preferably 3-40 times, more preferably 5-30 times and most preferably 8-25 times.

The grinding media can consist e.g. essentially of $Al_2O_3$, $Si_3N_4$, $TiO_2$, WC (tungsten carbide) or of $ZrO_2$ or a combination of those compounds. Most preferably $ZrO_2$-type grinding media like $ZrO_2$ stabilized with $Y_2O_3$ are used.

The aqueous nanosuspension which is processed can have a solids content of up to 25% or even more.

In a preferred embodiment of the invention the water is removed as much as possible by choosing suitable drying conditions, and the water content is lower than e.g. 10%.

All measurements of particle size referred to in this specification are made by laser diffraction technique using a "Mastersizer 2000" of Malvern Instruments Ltd., UK.

The following examples are illustrative only but are not intended to limit the scope of the invention.

EXAMPLE 1

A starch sodium octenyl succinate solution (46%) was prepared by dissolving starch sodium octenyl succinate (490 g) available at the National Starch and Chemical Company, New Jersey, US under the product name Capsul, which had a moisture content of 8%, in 80° C. deionized water (490 g).

Genistein powder (20 g) was mixed with the starch sodium octenyl succinate solution (391.4 g) and deionized water (390 g) and passed through a high pressure homogenizer equipped with a 130-micron nozzle; DeBEE 2000, B.E.E. International Ltd., Israel, which had about 200 g of water in the pipeline, at a homogenization pressure of 1500 bar. The back pressure was set at 120 bar during homogenization. The genistein suspension after the nozzle was cooled to about 20 to 30° C. with a heat exchanger. The suspension, with a solid content of about 20%, was cycled through the homogenizer 42 times until the desired particle size was reached. The genistein particle size was determined by laser diffraction technique (Mastersizer 2000, Malvern Instruments Ltd., UK) and the results, calculated based on the refractive index of 1.469, are shown below in Table I.

TABLE I

Particle size measurements of genistein

|  | Genistein particle size before homogenization | Genistein particle size after homogenization (42 passes) |
|---|---|---|
| D (v, 0.1) | 17.1 microns | 0.07 microns |
| D (v, 0.5) | 41.9 microns | 0.17 microns |
| D (v, 0.9) | 91.0 microns | 3.65 microns |
| Average particle size D[4, 3]: | 48.5 microns | 0.97 microns |
| Average particle size D[3, 2]: | 23.1 microns | 0.15 microns |

The homogenized genistein suspension was dried with a Niro spray dryer (GEA Niro A/S, Denmark) with a nozzle pressure of 4 bar. The inlet temperature was about 200° C. and outlet temperature was about 80° C. The spray-dry powder contained approximate 9.4% genistein with a moisture content of 5.87%. The genistein particle size was determined by re-dispersing the spray-dry powder in water and measured by the laser diffraction technique and the results are shown in Table II.

TABLE II

Particle size measurements of Spray-dried genistein form

|  | Genistein particle size after homogenization (42 passes) and spray-drying |
|---|---|
| D (v, 0.1) | 0.07 microns |
| D (v, 0.5) | 0.16 microns |
| D (v, 0.9) | 2.86 microns |
| Average particle size D[4, 3] | 0.83 microns |
| Average particle size D[3, 2] | 0.14 microns |

EXAMPLE 2

Genistein powder (30 g) was mixed with deionized water (370 g) and passed through a high-pressure homogenizer (equipped with a 130-micron nozzle; DeBEE 2000, BEE International, Israel), which had about 200 g of water in the pipeline, at a homogenization pressure of 1500 bar. The back pressure was set at 120 bar during homogenization. The genistein suspension after the nozzle was cooled to about 20 to 30° C. with a heat exchanger. The suspension, with a solid content of about 5%, was cycled through the homogenizer 40 times until the desired particle size was reached. The genistein particle size was determined by laser diffraction technique (Mastersizer 2000, Malvern Instruments Ltd., UK), and the results, calculated based on the refractive index of 1.469, are shown below in Table III.

TABLE III

Particle size measurements of genistein

|  | Genistein particle size before homogenization | Genistein particle size after homogenization (40 passes) |
|---|---|---|
| D (v, 0.1) | 17.1 microns | 0.07 microns |
| D (v, 0.5) | 41.9 microns | 0.16 microns |
| D (v, 0.9) | 91.0 microns | 2.42 microns |
| Average particle size D[4, 3] | 48.5 microns | 0.76 microns |
| Average particle size D[3, 2] | 23.1 microns | 0.14 microns |

A starch sodium octenyl succinate solution (46%) was prepared by dissolving starch sodium octenyl succinate (490 g), which had a moisture content of 8%, in 80° C. deionized water (490 g). A portion of the starch sodium octenyl succinate solution (65 g) was added to the homogenized genistein suspension in the feed funnel at the end of the 40th pass without stopping the homogenization process, and the mixture (approx. 9% solid) was passed through the high pressure homogenizer twice. The genistein particle size was determined by laser diffraction technique (Mastersizer 2000, Malvern Instruments Ltd., UK), and the results are shown below in Table IV.

TABLE IV

Particle size measurements of genistein

|  | Genistein particle size after homogenization (42 passes) |
|---|---|
| D (v, 0.1) | 0.07 microns |
| D (v, 0.5) | 0.16 microns |
| D (v, 0.9) | 0.93 microns |
| Average particle size D[4, 3] | 0.41 microns |
| Average particle size D[3, 2] | 0.14 microns |

The homogenized genistein suspension was dried with a Niro spray dryer (GEA Niro A/S, Denmark) with a nozzle pressure of 4 bar. The inlet temperature was about 200° C. and outlet temperature was about 80° C. The spray-dry powder contained approximately 48.5% genistein with a moisture content of 3.24%. The genistein particle size was determined by re-dispersing the spray-dry powder in water and measured by the laser diffraction technique. The results are shown in Table V.

TABLE V

Particle size measurements of Spray-dried genistein form

| | Genistein particle size after homogenization (42 passes) and spray-drying |
|---|---|
| D (v, 0.1) | 0.07 microns |
| D (v, 0.5) | 0.15 microns |
| D (v, 0.9) | 1.14 microns |
| Average particle size D[4, 3] | 0.55 microns |
| Average particle size D[3, 2] | 0.14 microns |

EXAMPLE 3

Genistein powder (36 g) was mixed with deionized water (364 g) and passed through a high-pressure homogenizer (equipped with a 130-micron nozzle; DeBEE 2000, BEE International, Israel), which had about 200 g of water in the pipeline, at a homogenization pressure of 1500 bar. The back pressure was set at 120 bar during homogenization. The genistein suspension after the nozzle was cooled to about 20 to 30° C. with a heat exchanger. The suspension, with a solid content of about 6%, was cycled through the homogenizer 40 times until the desired particle size was reached. The genistein particle size was determined by laser diffraction technique (Mastersizer 2000, Malvern Instruments Ltd., UK), and the results, calculated based on the refractive index of 1.469, are shown below in Table VI.

TABLE VI

Particle size measurements of genistein

| | Genistein particle size before homogenization | Genistein particle size after homogenization (40 passes) |
|---|---|---|
| D (v, 0.1) | 17.1 microns | 0.07 microns |
| D (v, 0.5) | 41.9 microns | 0.16 microns |
| D (v, 0.9) | 91.0 microns | 2.00 microns |
| Average particle size D[4, 3] | 48.5 microns | 0.76 microns |
| Average particle size D[3, 2] | 23.1 microns | 0.14 microns |

A starch sodium octenyl succinate solution (46%) was prepared by dissolving starch sodium octenyl succinate (490 g), which had a moisture content of 8%, in 80° C. deionized water (490 g). A portion of the starch sodium octenyl succinate solution (19.5 g) was added to the homogenized genistein suspension in the feed funnel at the end of the 40th pass without stopping the homogenization process, and the mixture (approx. 7.3% solid) was passed through the high pressure homogenizer twice. The genistein particle size was determined by laser diffraction technique (Mastersizer 2000, Malvern Instruments Ltd., UK), and the results are shown below in Table VII.

TABLE VII

Particle size measurements of genistein

| | Genistein particle size after homogenization (42 passes) |
|---|---|
| D (v, 0.1) | 0.07 microns |
| D (v, 0.5) | 0.16 microns |
| D (v, 0.9) | 0.91 microns |
| Average particle size D[4, 3] | 0.40 microns |
| Average particle size D[3, 2] | 0.14 microns |

The homogenized genistein suspension was dried with a Niro spray-dryer (GEA Niro A/S, Denmark) with a nozzle pressure of 4 bar. The inlet temperature was about 200° C. and outlet temperature was about 80° C. The spray-dry powder contained approximately 78.2% genistein with a moisture content of 2.31%. The genistein particle size was determined by re-dispersing the spray-dry powder in water and measured by the laser diffraction technique. The results are shown below in Table VIII.

TABLE VIII

Particle size measurements of Spray-dried genistein form

| | Genistein particle size after homogenization (42 passes) and spray-drying |
|---|---|
| D (v, 0.1) | 0.07 microns |
| D (v, 0.5) | 0.16 microns |
| D (v, 0.9) | 0.97 microns |
| Average particle size D[4, 3] | 0.43 microns |
| Average particle size D[2, 3] | 0.14 microns |

EXAMPLE 4

Genistein powder (120 g) was mixed with deionized water (280 g) and passed through a high-pressure homogenizer (equipped with a 180-micron nozzle; DeBEE 2000, BEE International, Israel), which had about 200 g of water in the pipeline, at a homogenization pressure of 700 bar. The back pressure was set at 120 bar during homogenization. The genistein suspension after the nozzle was cooled to about 20 to 30° C. with a heat exchanger. The suspension, with a solid content of about 20%, was cycled through the homogenizer 20 times until the desired particle size was reached. The genistein particle size was determined by laser diffraction technique (Mastersizer 2000, Malvern Instruments Ltd., UK), and the results, calculated based on the refractive index of 1.469, are shown below in Table IX.

TABLE IX

Particle size measurements of genistein

| | Genistein particle size before homogenization | Genistein particle size after homogenization (20 passes) |
|---|---|---|
| D (v, 0.1) | 17.1 microns | 0.07 microns |
| D (v, 0.5) | 41.9 microns | 0.15 microns |
| D (v, 0.9) | 91.0 microns | 2.62 microns |
| Average particle size D[4, 3] | 48.5 microns | 0.83 microns |
| Average particle size D[3, 2] | 23.1 microns | 0.13 microns |

EXAMPLE 5

Genistein powder (36 g) was mixed with deionized water (364 g) and passed through a high-pressure homogenizer (equipped with a 130-micron nozzle; DeBEE 2000, BEE International, Israel), which had about 200 g of water in the pipeline, at a homogenization pressure of 1500 bar. The back pressure was set at 120 bar during homogenization. The genistein suspension after the nozzle was cooled to about 20 to 30° C. with a heat exchanger. The suspension, with a solid content of about 6%, was cycled through the homogenizer 40 times until the desired particle size was reached. The genistein particle size was determined by laser diffraction technique (Mastersizer 2000, Malvern Instruments Ltd., UK), and the results, calculated based on the refractive index of 1.469, are shown below in Table X.

TABLE X

Particle size measurements of genistein

|   | Genistein particle size before homogenization | Genistein particle size after homogenization (20 passes) |
|---|---|---|
| D (v, 0.1) | 17.8 microns | 0.07 microns |
| D (v, 0.5) | 41.4 microns | 0.16 microns |
| D (v, 0.9) | 90.2 microns | 0.92 microns |
| Average particle size D[4, 3] | 48.5 microns | 0.42 microns |
| Average particle size D[2, 3] | 23.1 microns | 0.14 microns |

A maltodextrin solution (45%; 52 g) was prepared by dissolving maltodextrin (25 g), which had a moisture content of 6.18%, in deionized water (27 g). A portion of the maltodextrin solution (19.5 g) was added to the homogenized genistein suspension in the feed funnel at the end of the 40th pass without stopping the homogenization process, and the mixture (approx. 7.3% solid) was passed through the high pressure homogenizer twice more. The genistein particle size was determined by laser diffraction technique (Mastersizer 2000, Malvern Instruments Ltd., UK), and the results are shown below in Table XI.

TABLE XI

Particle size measurements of Spray-dried genistein form

|   | Genistein particle size after homogenization (42 passes) and spray-drying |
|---|---|
| D (v, 0.1) | 0.07 microns |
| D (v, 0.5) | 0.16 microns |
| D (v, 0.9) | 0.93 microns |
| Average particle size D[4, 3] | 0.41 microns |
| Average particle size D[3, 2] | 0.14 microns |

The homogenized genistein suspension was dried with a Niro spray-dryer (GEA Niro A/S, Denmark) with a nozzle pressure of 4 bar. The inlet temperature was about 200° C. and outlet temperature was about 80° C. The spray-dry powder contained approximately 78.2% genistein. The genistein particle size was determined by re-dispersing the spray-dry powder in water and measured by the laser diffraction technique. The results are shown below in Table XII.

TABLE XII

Particle size measurements of Spray-dried genistein form

|   | Genistein particle size after homogenization (42 passes) and spray-drying |
|---|---|
| D (v, 0.1) | 0.07 microns |
| D (v, 0.5) | 0.15 microns |
| D (v, 0.9) | 0.93 microns |
| Average particle size D[4, 3] | 0.41 microns |
| Average particle size D[3, 2] | 0.13 microns |

EXAMPLE 6

A starch sodium octenyl succinate solution (30%) was prepared by dissolving Capsul (2.8 kg; National Starch and Chemical Company, New Jersey, US), which had a moisture content of 8%, in 70° C. deionized water (5.7 kg).

Genistein powder (3.0 kg) was mixed with the starch sodium octenyl succinate solution (8.5 kg) and deionized water (9.0 kg) and passed through an agitated bead mill (Netzsch type LMZ 4; Netzsch GmbH & Co. Holding KG, Selb, Germany) rotating with 1150 Upm using 0.4 mm $ZrO_2$-type grinding media consisting of $ZrO_2$ stabilized with $Y_2O_3$. The genistein suspension after the agitated bead mill was cooled to 40-45° C. with a heat exchanger. The suspension with a solid content of about 27% was cycled through the agitated bead mill for 2 hours (11 cycles over the mill) until the desired particle size was reached.

The genistein particle size was determined by laser diffraction technique (Mastersizer 2000, Malvern Instruments Ltd., UK) and the results, calculated based on the refractive index of 1.469, are shown below in Table XIII.

TABLE XIII

Particle size measurements of genistein

|   | Genistein particle size before homogenization | Genistein particle size after homogenization (11 passages) |
|---|---|---|
| D (v, 0.1) | 17.8 microns | 0.07 microns |
| D (v, 0.5) | 41.4 microns | 0.16 microns |
| D (v, 0.9) | 90.2 microns | 0.45 microns |
| Average particle size D[4, 3]: | 48.5 microns | 0.23 microns |

The homogenized genistein suspension can be spray used for the target application field or can be spray dried using the procedure described in example 2.

EXAMPLE 7

Genistein powder (6 kg) is milled in a Jet mill by a dry grinding process. Suitable mill: Alpine 100 AFG by Hosokawa Alpine company using a jet pressure of 5.0 bar and speed of the sifter wheel of 20.000 Upm. This genistein is used in the "swing" test shown in FIG. 7 for comparative reasons.

A starch sodium octenyl succinate solution (48%) was prepared by dissolving starch sodium octenyl succinate (6.0 kg; National Starch and Chemical Company, New Jersey, US), which had a moisture content of 8%, in 70° C. deionized water (6.1 kg).

The milled genistein powder (6.0 kg) was mixed with the starch sodium octenyl succinate solution (12.1 kg) and deionized water (24 kg) and passed through a high pressure homogenizer equipped with a mixing device as described in EP 1 008 380 A2 at a homogenization pressure of 700 bar. The genistein suspension after the nozzle was cooled to about 20 to 30° C. with a heat exchanger. The suspension, with a solid content of about 20%, was cycled through the homogenizer 12 times until the desired particle size was reached (final genistein). As illustrated by FIG. 8. The genistein particle size was determined by laser diffraction technique (Mastersizer 2000, Malvern Instruments Ltd., UK) and the results, calculated based on the refractive index of 1.469, are shown below in Table XIV.

TABLE XIV

Particle size measurements of genistein

|  | Genistein particle size before milling and homogenization | Genistein particle size after milling and homogenization |
| --- | --- | --- |
| D (v, 0.1) | 17.8 microns | 0.07 microns |
| D (v, 0.5) | 41.4 microns | 0.18 microns |
| D (v, 0.9) | 90.2 microns | 1.38 microns |
| Average particle size D[4, 3]: | 48.5 microns | 0.53 microns |

The genistein after homogenization was also used in the "swing" test, and the result is shown in FIG. 8.

The homogenized dispersion was spray dried with a Multi Stage Spray dryer with a nozzle pressure of at about 40 bar. The inlet temperature was about 160° C., the outlet temperature was about 80° C. and the inlet air temperature of the internal fluid bed was about 50° C. The genistein particle size was determined by laser diffraction technique (Mastersizer 2000, Malvern Instruments Ltd., UK) and the results, calculated based on the refractive index of 1.469, are shown below in Table XV.

TABLE XV

Particle size measurements of genistein

|  | Genistein particle size before milling and homogenization | Genistein particle size after milling, homogenization and spray drying |
| --- | --- | --- |
| D (v, 0.1) | 17.8 microns | 0.08 microns |
| D (v, 0.5) | 41.4 microns | 0.19 microns |
| D (v, 0.9) | 90.2 microns | 1.84 microns |
| Average particle size D[4, 3]: | 48.5 microns | 0.65 microns |

EXAMPLE 8

O/W Emulsions with Different Genistein Forms

| Ingredients | #1 % (w/w) | #2 % (w/w) |
| --- | --- | --- |
| Glyceryl Myristate | 5.00 | 4.00 |
| Cetyl Alcohol | 2.00 | 2.00 |
| Steareth-2 | 2.00 | 2.00 |
| Steareth-21 | 2.00 | 2.00 |
| Isopropyl Myristate | 10.00 | 5.00 |
| Caprylic/Capric Triglyceride |  | 8.00 |
| BHT | 0.05 | 0.05 |
| Dimethicone | — | 2.00 |
| Phenoxyethanol & Methylparaben & Ethylparaben & Butylparaben & Propylparaben & Isobutylparaben | 0.80 | 0.80 |
| Aqueous suspension of genistein nanoparticles (contains 5.5% genistein, approx. 0.4 microns) | 5.00 | — |
| Genistein (crystalline, approx. 12 microns) | — | 0.10 |
| Water | Ad. 100 | Ad. 100 |
| Polysorbate 20 |  | 1.00 |
| Propylene Glycol | 5.00 | 4.00 |
| Ethoxydiglycol | 8.00 | 10.00 |
| Polyacrylamide & C13-14 Isoparaffin & Laureth-7 | 2.00 | 1.00 |
| Triethanol Amine (10%) | 0.33 | 0.29 |
| Disodium EDETA | 0.10 | 0.10 |

Figure 2:
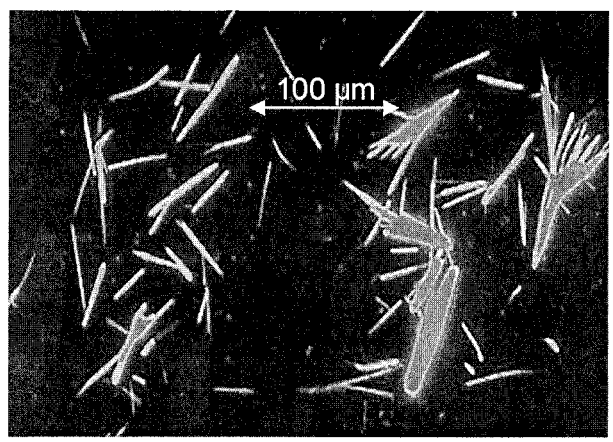
FIG. 2 is a microscopial examination of formulation #2 below with conventional crystalline genistein after 6 months at room temperaature.

The advantage of using the genistein form consisting of nanoparticles versus the conventional crystalline form in typical cosmetic formulations is illustrated by FIG. 1 and FIG. 2. Cosmetic formulations containing active ingredients should be stable upon storage at different temperatures for at least one year at room temperature. One important parameter monitored in a stability watch is the appearance of the cosmetic formulation under a microscope. Cosmetic formulations containing difficult to solubilize active ingredients will very often develop crystals upon storage, sometimes just within a few days. This phenomenon is even more pronounced by observing formulations which were stored at 5° C. There are many drawbacks with formulations which have developed such large crystals as illustrated in FIG. 2, which shows a microscopical examination of formulation #2 with conventional crystalline genistein after 6 months storage at room temperature, namely the reduced bioavailability of the active ingredient to the skin and the risk for the cosmetic consumer to perceive their presence upon application to the skin. As illustrated by FIG. 1, which shows a microscopical examination of formulation #1 with stabilized nanoparticles of genistein after 6 months storage at room temperature, the same cosmetic preparation with stabilized nanoparticles of genistein is perfectly stable, even after storage of 6 months at room temperature.

EXAMPLE 9

O/W Emulsions with Different Genistein Forms

| Ingredients | #3 % (w/w) | #4 % (w/w) |
| --- | --- | --- |
| Glyceryl Myristate | 4.00 | 4.00 |
| Cetyl Alcohol | 2.00 | 2.00 |
| Steareth-2 | 2.00 | 2.00 |
| Steareth-21 | 2.00 | 2.00 |
| Isopropyl Myristate | 5.00 | 5.00 |
| Caprylic/Capric Triglyceride | 8.00 | 8.00 |
| BHT | 0.05 | 0.05 |
| Dimethicone | 2.00 | 2.00 |
| Phenoxyethanol & Methylparaben & Ethylparaben & Butylparaben & Propylparaben & Isobutylparaben | 0.80 | 0.80 |
| Aqueous suspension of genistein nanoparticles (contains 5.5% genistein, approx. 0.4 microns) | 5.45 | — |
| Genistein (crystalline, approx. 12 microns) | — | 0.30 |
| Water | Ad. 100 | Ad. 100 |
| Propylene Glycol | 4.00 | 4.00 |

-continued

| Ingredients | #3 % (w/w) | #4 % (w/w) |
|---|---|---|
| Polyacrylamide & C13-14 Isoparaffin & Laureth-7 | 1.00 | 1.00 |
| Potassium Hydroxide (10%) | 0.15 | 0.15 |
| Disodium EDETA | 0.10 | 0.10 |

Figure 3:
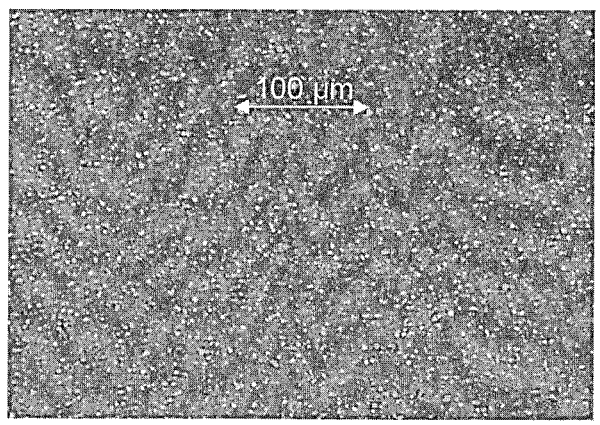
FIG. 3 is a microscopial examination of formulation #3 below with stabilized nanoparticles of genistein after 19 days storage at 5° C./43° C. (cycles of 24 hours at each temperature)

To further illustrate the benefits obtained with nanoparticles of genistein versus conventional crystalline genistein, the cosmetic formulations described above (#3 and #4) were submitted to a very challenging stability test: The formulations were stored at a temperature varying from 5° C. to 43° C. every 24 hours during 3 weeks. The appearance of the formulations was observed under a microscope and is illustrated by FIG. 3, which shows a microscopical examination of formulation #3 with stabilized nanoparticles of genistein after 19 days storage at 5° C./43° C. (cycles of 24 hours at each temperature), and FIG. 4, which shows a microscopical examination of formulation #4 with conventional crystalline genistein after 19 days storage at 5° C./43° C. (cycles of 24 hours at each temperature).

Figure 4:
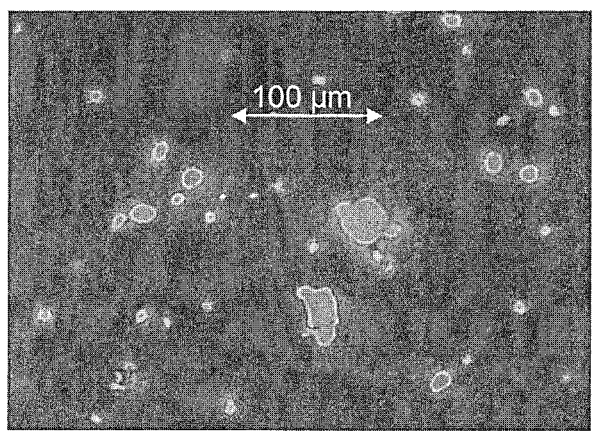
FIG. 4 is a microscopial examination of formulation #4 below with conventional crystalline genistein after 19 days storage at 5° C./43° C. (cycles of 24 hours at each temperature)

As illustrated by FIG. 3 the nanoparticles of genistein are still very finely dispersed in the cosmetic preparation, contrary to FIG. 4 which illustrates that conventional crystalline genistein in the same preparation has formed large crystals.

EXAMPLE 10

To force the crystallization in a disperse system, a test was used in which the temperature is changed over a self-defined timeframe and in self-defined sequences. The test is called "swing" test (changing temperature test). The purpose of this test is to dissolve small particles at the higher temperature and to force re-crystallization at lower temperature. But it is also a stress testing method which shows if a formulation is stable. The following formulations were used for the "swing" test:

| Pos. | Ingredient | Content |
|---|---|---|
| o | Caprylic/Capric Triglyceride | 8.00% |
| o | Isopropyl Myristate | 5.00% |
| o | Glyceryl Myristate | 4.00% |
| o | Cetyl Alcohol | 2.00% |
| o | Dimethicone | 2.00% |
| o | Steareth-2 | 2.00% |
| o | Steareth-21 | 2.00% |
| o | Phenoxyethanol & Methylparaben & Ethylparaben & Butylparaben | 0.80% |
| o | BHT | 0.05% |
| w | Water dem. | ad 100% |
| w | Propylene Glycol | 4.00% |
| w | Edeta BD | 0.10% |
| t | Polyacrylamide & C13-14 Isoparaffin & Laureth-7 | 1.00% |
| g | Genistein | 0.1%-1.0% |
| b | Potassium Hydroxide 10% solution | 0.15% |

Manufacturing Specifications:

Oil- and water phase (o+w) were separately heated up to 70° C. (±5° C.) and were added together. The thickening agent (t) was added under moderate agitation. The mixture was homogenized for 30 seconds at 24,000 RPM by means of an Ultra-Turrax T25 homogenizer. The emulsion was cooled down slowly to 45° C.±5° C. under moderate stirring (horseshoe mixer, 120 RPM). At this temperature the pH value was adjusted to pH 6.5-7.0 by adding base (b). Genistein (g) was added to the still fluid emulsion and was incorporated by homogenizing again for 30 sec. 24,000 RPM by means of an Ultra-Turrax T25 homogenizer. The formulation was cooled down to 25° C.±5° C. under moderate stirring (horseshoe mixer, 120 RPM).

Standard Stability Assessment:

As a standard stability test the following conditions were used: the formulated cosmetic samples were stored: 5° C.±2° C., ambient temperature (e.g. 20-25° C.) and 43° C.±2° C. with checkpoints after 2 weeks, 6 weeks, 3 months, 6 months and 12 months. A few samples show crystal growth not before 3 months, which means that a long period goes by where no statement of future morphologic stability can be made.

Stability Assessment by "Swing" Test:

To force this crystallization the "swing" test was used and as minimum and maximum temperatures 5° C. and 43° C. were chosen. Each temperature was held over a period of 24 hours. The duration of this test was at first set to 20 days, which means that the samples run through a cooling/heating sequence (=1 sequence) 10 times.

Figure 5A:
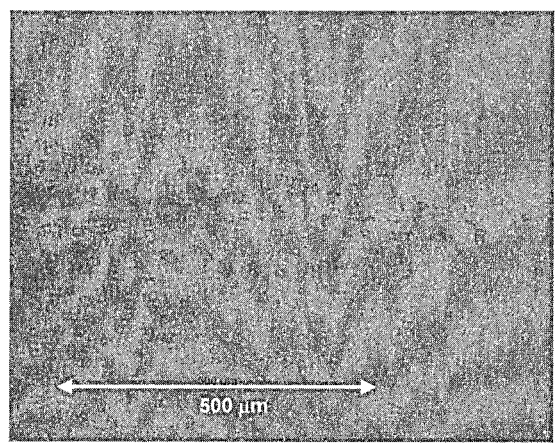
FIGS. 5(a) to 8(c) show the results of "swing" tests for genistein-containing emulsions using the genistein nanoparticle compositions as described below, wherein magnification was the same in all figures, and a distance of 500 µm is indicated in FIG. 5(a).

FIGS. 5 to 7 show the results of the "swing" test. Genistein-containing emulsions where prepared as described above using the genistein nanoparticle compositions as described below. The following genistein samples and concentrations were employed and the emulsions were measured immediately after preparation and after subjecting the samples to ten sequences of the "swing" test:

FIG. 5(a): Composition of example 3 in a concentration of 0.3%

Figure 5B:
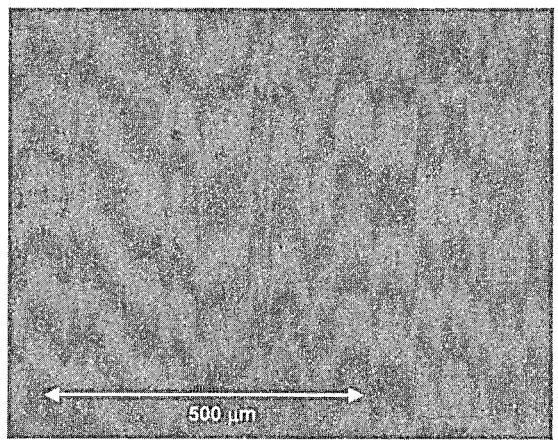

FIG. 5(b): Composition of example 3 in a concentration of 0.5%

Figure 5C:
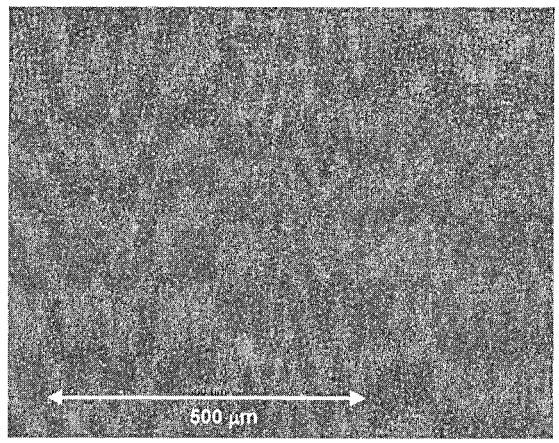

FIG. 5(c): Composition of example 3 in a concentration of 1.0%

Figure 6A:
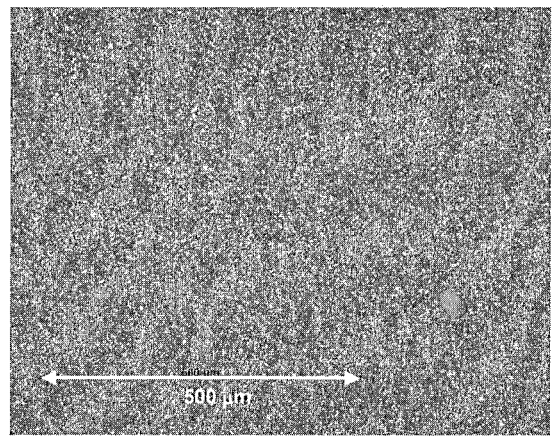

FIG. 6(a): Composition of example 6 in a concentration of 0.3%

Figure 6B:
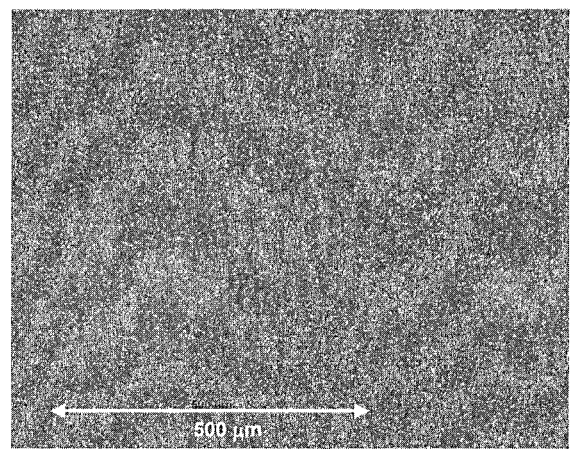

FIG. 6(b): Composition of example 6 in a concentration of 0.5%

Figure 6C:
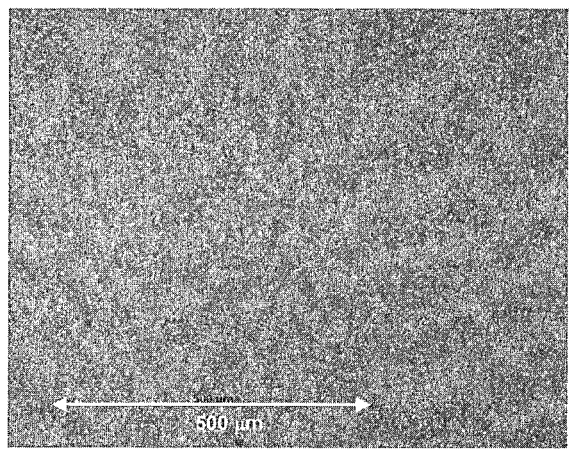

FIG. 6(c): Composition of example 6 in a concentration of 1.0%

Figure 7A:
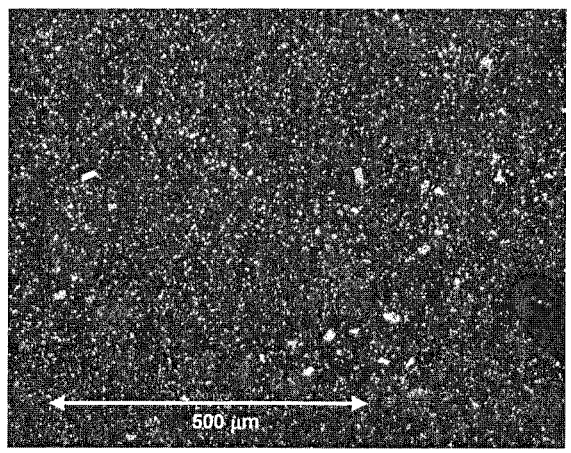

FIG. 7(a): Composition of example 7, after dry grinding in a Jet mill in a concentration of 0.3%

Figure 7B:
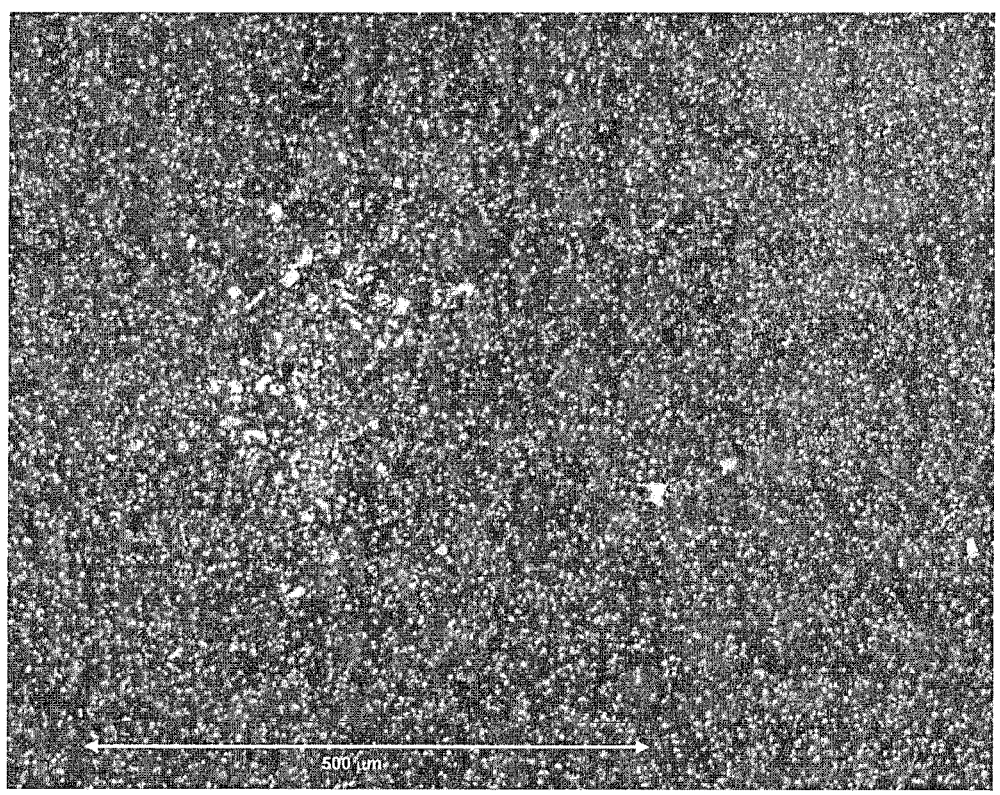

FIG. 7(b): Composition of example 7 after dry grinding in a Jet mill in a concentration of 0.5%

Figure 7C:
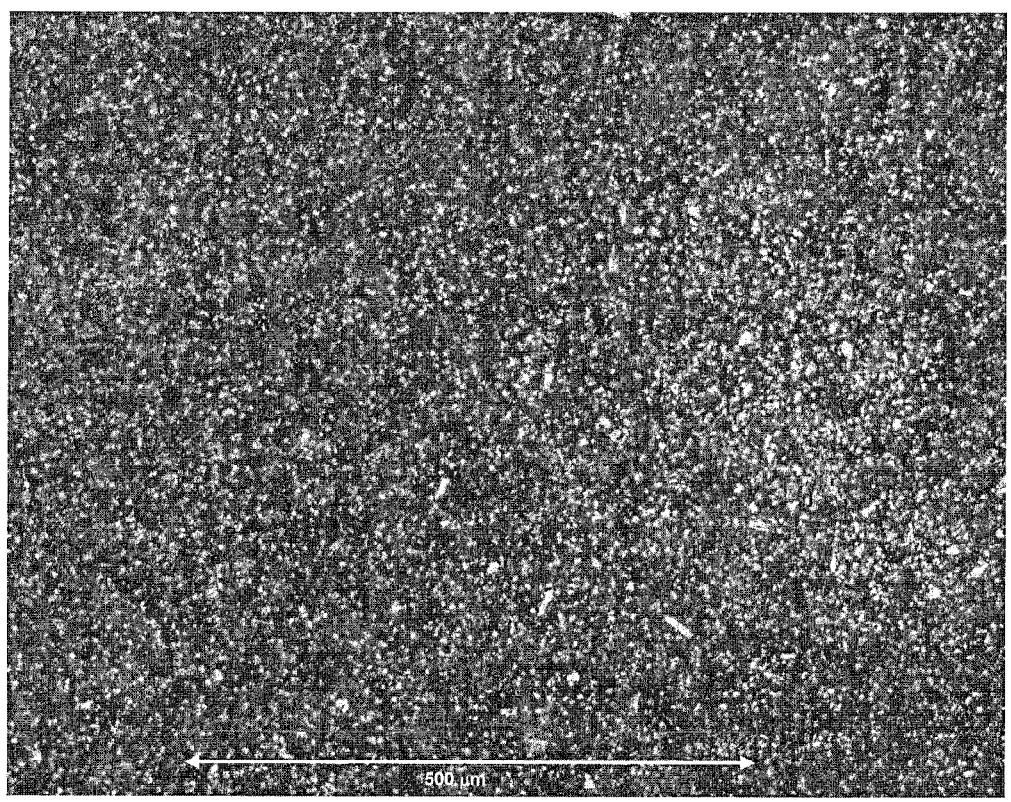

FIG. 7(c): Composition of example 7 after dry grinding in a Jet mill in a concentration of 0.1%

Figure 8A:
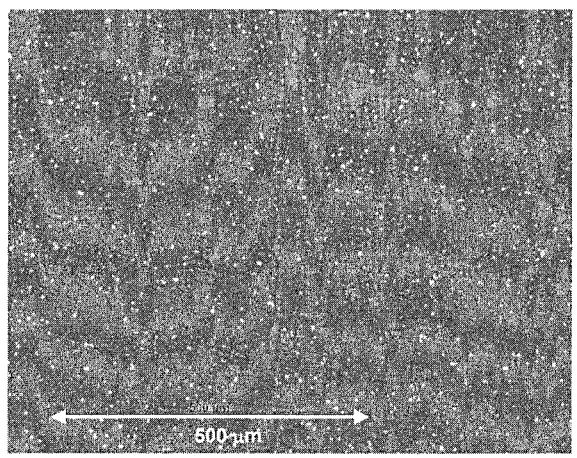

FIG. 8(a): Composition of example 7 final product as described in example 7 in a concentration of 0.3%

Figure 8B:
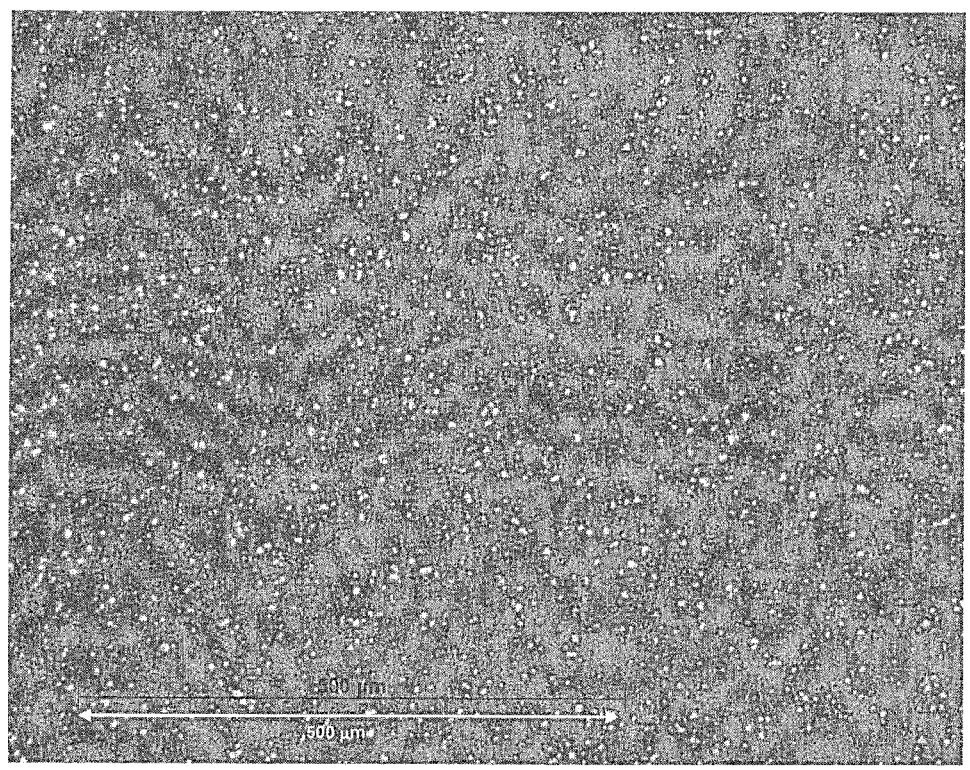

FIG. 8(b): Composition of example 7 final product as described in example 7 in a concentration of 0.5%

Figure 8C:
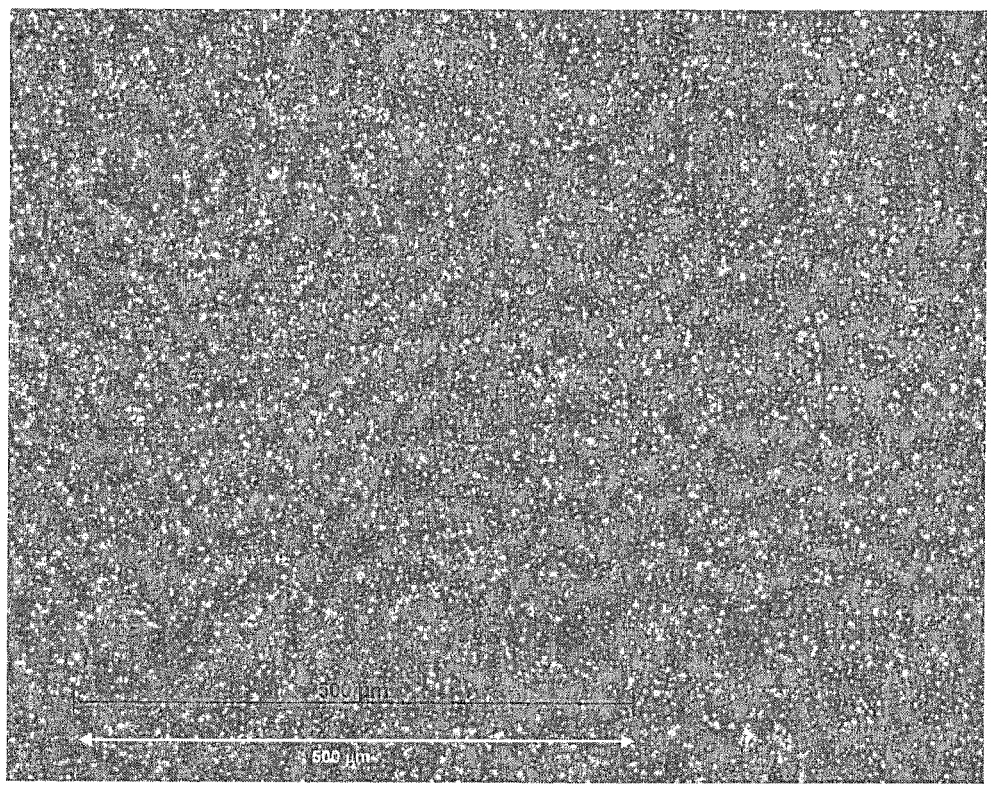

FIG. 8(c): Composition of example 7 final product as described in example 7 in a concentration of 1.0%.

The magnification was the same in all figures, and a distance of 500 μm is indicated in FIG. 5(a).

It can be seen that even under the severe conditions of the "swing" test the topical cosmetic compositions of the present invention do not show any increase in the particle size, even in very high concentrations of 0.3 to 1.0%. The "swing" test in fact had no effect on the particle size or the particle distribution.

Contrary thereto, in FIG. 7, where genistein was used before milling or homogenization, the particle size significantly changed during the "swing" test. Huge crystals are formed and clusters of crystals can be seen after ten sequences.

The invention claimed is:

1. An isoflavone nanoparticle composition, comprising an isoflavone, a carbohydrate carrier and optionally water, wherein the isoflavone has an average particle size D[4.3] as determined by laser diffraction technique of less than 3 µm, and wherein the carbohydrate carrier is a hydrophobically modified starch.

2. The isoflavone nanoparticle composition according to claim 1, wherein the isoflavone is genistein.

3. The isoflavone nanoparticle composition according to claim 1, wherein the isoflavone has an average particle size D[4.3] as determined by laser diffraction technique of 1 micron or less.

4. The isoflavone nanoparticle composition according to claim 3, wherein the isoflavone has an average particle size D[4.3] as determined by laser diffraction technique of 0.5 micron or less.

5. The isoflavone nanoparticle composition according to claim 1, wherein the isoflavone has an average particle size D[4.3] as determined by laser diffraction technique of 0.05 micron or more.

6. The isoflavone nanoparticle composition according to claim 1, wherein the composition is a powder or granular composition.

7. The isoflavone nanoparticle composition according to claim 6, wherein the composition comprises at least 1 wt.-% isoflavone.

8. The isoflavone nanoparticle composition according to claim 7, wherein the composition comprises at least 20 wt.-% isoflavone.

9. The isoflavone nanoparticle composition according to claim 8, wherein the composition comprises at least 70 wt.-% isoflavone.

10. The isoflavone nanoparticle composition according to claim 1, wherein the composition is an aqueous suspension.

11. The isoflavone nanoparticle composition according to claim 10, consisting of 10 to 30% of isoflavone, 15 to 40% of carrier and the rest being water.

12. A process for producing an isoflavone nanoparticle composition according to claim 1, comprising subjecting crystalline isoflavone, water and a carrier to high pressure homogenization until a particle size of less than 3 µm as determined by laser diffraction is achieved thereby obtaining a suspension thereof, and optionally subjecting the resulting suspension to a drying process.

13. The process according to claim 12, wherein the drying process is spray drying or freeze drying.

14. The process according to claim 12, wherein the isoflavone is prehomogenized in water prior to mixing and homogenizing it with the carrier.

15. The process according to claim 12, wherein the isoflavone is subjected to high pressure homogenization in the presence of the carrier at a pressure from 500 bar to 4000 bar.

16. A process for producing an isoflavone nanoparticle composition according to claim 1, comprising subjecting a mixture comprising isoflavone, water and a carrier to a wet grinding process in an agitated bead mill until a particle size of less than 3 µm as determined by laser diffraction is achieved thereby obtaining a suspension thereof, and optionally subjecting the resulting suspension to a drying process.

17. The process according to claim 16, wherein the isoflavone and optionally the carrier are cycled 1 to 50 times through the agitated bead mill.

18. The process according to claim 16, wherein $ZrO_2$-type grinding media are used in the wet grinding process.

19. A pharmaceutical composition comprising an isoflavone nanoparticle composition as claimed in claim 1.

20. The pharmaceutical composition according to claim 19, which contains the isoflavone in a concentration of 0.05 to 50 wt.-%.

21. A nutritional product comprising an isoflavone nanoparticle composition claim 1.

22. The nutritional product according to claim 21, which is selected from tofu, yogurt and fruit juices.

23. The isoflavone nanoparticle composition according to claim 1, wherein the carrier comprises starch sodium octenyl succinate.

24. A cosmetic composition comprising an isoflavone nanoparticle composition as claimed in claim 1.

25. The cosmetic composition according to claim 24, which contains the isoflavone in a concentration of 0.05 to 50 wt.-%.

* * * * *